(12) United States Patent
Randles et al.

(10) Patent No.: US 10,748,451 B2
(45) Date of Patent: Aug. 18, 2020

(54) METHODS AND SYSTEMS FOR GENERATING FLUID SIMULATION MODELS

(71) Applicants: The Brigham and Women's Hospital, Inc., Boston, MA (US); Duke University, Durham, NC (US)

(72) Inventors: Amanda Randles, Durham, NC (US); Jane Leopold, Boston, MA (US)

(73) Assignees: DUKE UNIVERSITY, Durham, NC (US); THE BRIGHAM AND WOMEN'S HOSPITAL, INC., Boston, MA (US)

(*) Notice: Subject to any disclaimer, the term of this patent is extended or adjusted under 35 U.S.C. 154(b) by 22 days.

(21) Appl. No.: 15/843,423

(22) Filed: Dec. 15, 2017

(65) Prior Publication Data

US 2018/0174490 A1 Jun. 21, 2018

Related U.S. Application Data

(60) Provisional application No. 62/434,565, filed on Dec. 15, 2016.

(51) Int. Cl.
| | | |
|---|---|---|
| *G06K 9/00* | (2006.01) | |
| *G09B 23/30* | (2006.01) | |
| *G06T 7/00* | (2017.01) | |
| *G06T 7/11* | (2017.01) | |
| *G06T 11/00* | (2006.01) | |

(Continued)

(52) U.S. Cl.
CPC .......... *G09B 23/303* (2013.01); *G06T 7/0014* (2013.01); *G06T 7/11* (2017.01); *G06T 11/003* (2013.01); *G06T 15/08* (2013.01); *G06T 17/00* (2013.01); *G16H 50/20* (2018.01); *G16H 50/50* (2018.01); *A61B 6/504* (2013.01); *G06T 2200/04* (2013.01); *G06T 2200/08* (2013.01); *G06T 2207/10081* (2013.01);

(Continued)

(58) Field of Classification Search
CPC ....... A61B 6/504; G06T 11/003; G06T 15/08; G06T 17/00; G06T 2200/04; G06T 2200/08; G06T 2207/10081; G06T 2207/30104; G06T 2210/24; G06T 2211/404; G06T 7/0014; G06T 7/11; G09B 23/286; G09B 23/303; G16H 50/20
See application file for complete search history.

(56) References Cited

U.S. PATENT DOCUMENTS

| | | | | |
|---|---|---|---|---|
| 2006/0036167 A1* | 2/2006 | Shina | ................... | A61B 6/12 600/433 |
| 2008/0091171 A1* | 4/2008 | Strommer | ............. | A61B 5/06 604/528 |

(Continued)

*Primary Examiner* — Xin Jia
(74) *Attorney, Agent, or Firm* — McDonnell Boehnen Hulbert & Berghoff LLP

(57) ABSTRACT

Systems and methods for generating three-dimensional fluid flow simulations from two-dimensional (2D) image data are provided. Data is segmented from 2D images of a sample having a biological structure with fluid flow therethrough. Three-dimensional (3D) geometries are generated from the segmented data, and then a 3D reconstruction of the biological structure is generated from the 3D geometries. This 3D geometric computational analysis tool can be used to evaluate fluid dynamics and hemodynamics in the context of the structure anatomy and geometry.

17 Claims, 6 Drawing Sheets

(51) Int. Cl.
    *G06T 15/08*     (2011.01)
    *G06T 17/00*     (2006.01)
    *G16H 50/20*     (2018.01)
    *G16H 50/50*     (2018.01)
    *A61B 6/00*     (2006.01)
    *G09B 23/28*     (2006.01)

(52) U.S. Cl.
    CPC ........... *G06T 2207/30104* (2013.01); *G06T 2210/24* (2013.01); *G06T 2211/404* (2013.01); *G09B 23/286* (2013.01)

(56) References Cited

U.S. PATENT DOCUMENTS

| | | | |
|---|---|---|---|
| 2014/0079304 A1* | 3/2014 | Foo | G06T 11/008 382/131 |
| 2014/0200867 A1* | 7/2014 | Lavi | G06F 19/321 703/2 |
| 2014/0228678 A1* | 8/2014 | Meyer | A61B 6/12 600/424 |

* cited by examiner

| Experimental Validation 3D Phantom Angiography ||
|---|---|
| Vessel Location | Distance (mm) |
| Left main bifurcation | 6.40 |
| LAD - stenosis | 1.77 |
| LAD at point of Diag1 branch | 1.44 |
| LAD crossing over the diagonal | 1.33 |
| A point in the mid-D1 branch | 1.72 |
| LCx-branch OM1 | 2.01 |
| LCx-branch OM2 | 0.68 |
| Distal OM1 | 3.34 |
| Distal OM2 | 5.99 |
| Mid LCx | 4.08 |
| Average Distance | 2.86 |

200

| Influence of Side Branches on Hemodynamics | | | |
|---|---|---|---|
| Model | Coronary Volume (ml) | Average Velocity (m/s) | Average ESS (Pa) |
| All vessels (A) | 1.90 | 0.02 | 0.61 |
| Main vessels (B) | 1.65 | 0.06 | 1.73 |
| LAD 3 (C) | 0.72 | 0.01 | 0.25 |
| LAD 2 (D) | 0.71 | 0.04 | 1.22 |
| LAD 1 (E) | 0.70 | 0.06 | 1.72 |
| LAD 0 (F) | 0.54 | 0.16 | 4.75 |

Figure 3

METHODS AND SYSTEMS FOR GENERATING FLUID SIMULATION MODELS

CROSS-REFERENCE TO RELATED APPLICATIONS

This application claims priority to U.S. Provisional Patent Application Ser. No. 62/434,565 filed on Dec. 15, 2016, which is hereby incorporated by reference in its entirety.

BACKGROUND

Atherosclerosis, a disease in which plaque builds inside the arteries, limits the flow of oxygen-rich blood to organs and other parts of the body. Atherosclerosis can affect any artery or vein in the body, including arteries or veins in the heart, brain, arms, legs, pelvis, and kidneys. As a result, diseases may develop in various parts of the body based on which arteries or veins are affected.

One example disease, atherosclerotic cardiovascular disease, is the leading global cause of death, accounting for more than 17.3 million deaths per year, and is expected to grow to more than 23.6 million by 2030. Regions of low and oscillatory shear stress in a blood vessel have been connected with regions in blood vessels that have or will develop atherosclerosis.

Hemodynamic profiles for patients with coronary artery disease could provide insight into the underlying mechanisms driving the disease. However, three-dimensional (3D) reconstructions of coronary vessels are needed for fluid dynamics simulations. Reconstructions can be obtained from intravascular ultrasound, and yet this method is used in only a fraction of invasive studies of the coronary arteries. Two-dimensional (2D) coronary angiograms are, by contrast, widely available for a large number of individuals; however, methods to derive 3D fluid flow information directly from 2D coronary angiogram data do not exist.

Fluid flow profiles within various other structures in the body could provide insight into underlying issues for certain pathologies as well, and again, 2D images are more widely available for such structures than 3D reconstructions.

SUMMARY

In accordance with the present invention, systems and methods are defined for generating a three-dimensional fluid flow simulation of a sample. In one example embodiment, the method comprises acquiring one or more two-dimensional images of a sample, wherein the sample comprises a biological structure having fluid flow therethrough, segmenting data from the one or more two-dimensional images, generating three-dimensional geometries from the segmented data, and generating a three-dimensional reconstruction of the biological structure from the three-dimensional geometries.

In one example embodiment, the fluid flow is a blood flow, and the biological structure is a biological vessel, such as a coronary artery for example.

The method may further comprise generating a three-dimensional wall shear stress (WSS) map for the biological vessel by applying a computational fluid dynamics (CFD) simulation to the three-dimensional reconstruction of the biological vessel. The method may comprise generating fluid quantities such as velocity, vorticity, and pressure of a fluid for example.

In one example embodiment, the two-dimensional images comprise a computerized tomography (CT) scan. In certain embodiments, the CT scan is a 2D coronary CT angiogram.

In some embodiments, segmenting the data further comprises partitioning the image into a plurality of sets of pixels and separating the plurality of sets of pixels based on a threshold.

The method may be used to diagnose, provide a prognosis, monitor treatment, or provide guidance in medical or surgical management for a vascular disorder of a subject.

In another example embodiment, a system for non-invasive fluid flow analysis is provided. The system includes a CT apparatus configured to generate two-dimensional images from living tissue and a non-transitory computer-readable medium having stored therein instructions executable to cause a computing device to perform functions to extract tissue motion from the generated images.

In certain embodiments, the functions comprise acquiring one or more two-dimensional images of a sample, wherein the sample comprises a biological structure, such as a biological vessel having fluid flow therethrough, segmenting data from the one or more two-dimensional images, generating three-dimensional geometries from the segmented data, and generating a three-dimensional reconstruction of the biological structure from the three-dimensional geometries.

These as well as other aspects and advantages of the synergy achieved by combining the various aspects of this technology, that while not previously disclosed, will become apparent to those of ordinary skill in the art by reading the following detailed description, with reference where appropriate to the accompanying drawings.

BRIEF DESCRIPTION OF THE FIGURES

FIG. 3 depicts a graph displaying the geometric topology between CTA and angiogram derived arterial models, in accordance with at least one example embodiment.

DETAILED DESCRIPTION

Figure 1:
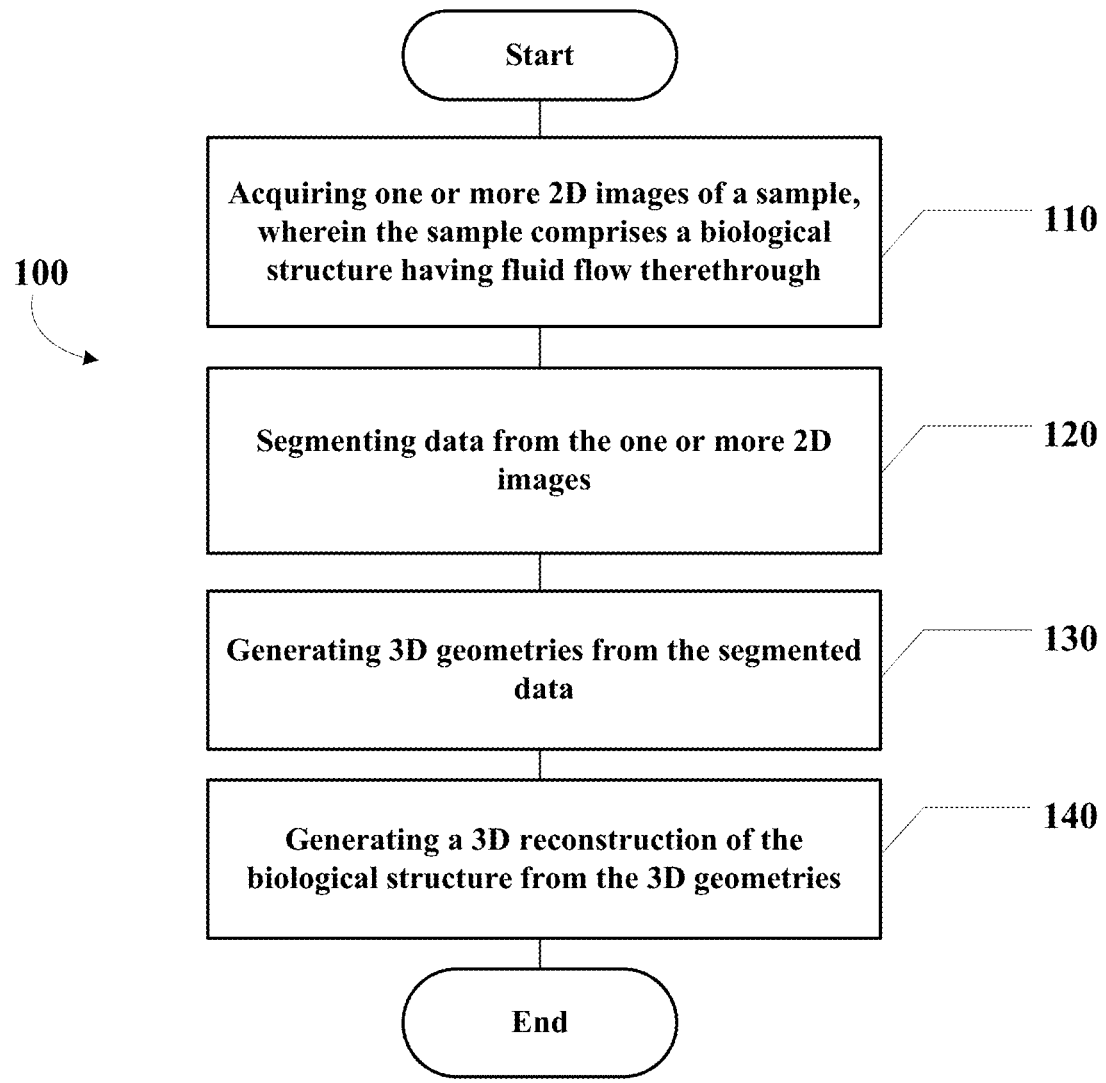
FIG. 1 depicts a simplified flow diagram of an example method that may be carried out to reconstruct a three-dimensional vascular geometry of a sample, in accordance with at least one example embodiment.

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. Unless otherwise defined, the technical terms used herein have the same meaning as commonly understood by one of ordinary skill in the art.

As used herein, the terms "subject" and "patient" are interchangeable and refer to both human and nonhuman animals. The term "nonhuman animals" includes all vertebrates, e.g., mammals and non-mammals. In certain embodiments, the subject is a human patient undergoing an angiogram. In certain embodiments, the subject suffers from, or is at risk of, a vascular disease.

As used herein, the term "about" provides for numerical values to fall slightly above or slightly below a given number or an endpoint of a numerical range without affecting the desired result.

I. Overview

Optical imaging provides for the noninvasive or invasive visualization of functional blood vessels and other structures through which fluid flows. Angiography is an optical imaging technique used to visualize the fluid flow through structures, such as lumen of blood vessels, including arteries and veins in the systemic and pulmonary circulations and the heart chambers as well as the lymphatic circulation.

Coronary angiography is a type of angiography, and is used to visualize lumens and diagnose blockages of the coronary arteries. Coronary angiography is performed by inserting a catheter in the femoral, brachial, or radial artery and guiding the catheter to the coronary blood vessels of the heart, then injecting a radiocontrast agent through the catheter to visualize the blood vessel lumen using fluoroscopic x-ray imaging. The images obtained by injecting radiocontrast dye are typically captured at 10-30 frames per second as motion images or films known as cineangiograms.

Angiography can be used to diagnose blockages in the arteries and veins and the lymphatic system. Using coronary angiography as an example, physicians assess the blockages in the coronary arteries either visually by estimating the percent reduction of the lumen diameter or using a tool called quantitative coronary angiography that uses edge detection to measure the diameter of the vessel lumen. This provides an anatomical assessment of the lesion, but it does not give an assessment of the functional significance of the stenosis, which is what is needed to proceed with revascularization.

For observed blockages that are considered intermediate (e.g., about 40-70% stenosis) or greater than 70% stenosis, an invasive test called fractional flow reserve (FFR) or instantaneous wave free ratio (IFR) analysis can be performed at the time of coronary angiography to determine whether the blockage is the cause of a patient's symptoms. For FFR, the patient is infused with adenosine to dilate the distal vessels, and pressure measurements are made. This procedure can determine if a stenosis requires revascularization by determining the pressure ratio before and after the stenosis with a ratio of less than or equal to about 0.80 requiring revascularization. For IFR, the procedure is the same with the exception of adenosine administration and revascularization is considered for a ratio of less than or equal to about 0.89. The decision to perform FFR vs. IFR is physician-dependent. Both procedures are necessary to proceed with revascularization but are associated with increased risk of adverse events for the patient. The adverse events include reaction to adenosine, major or minor bleeding, vessel perforation, vessel tearing, renal dysfunction or failure, myocardial infarction, arrhythmia, stroke, and even death.

In addition to using angiography to diagnose blockages, physicians can also insert a variety of imaging instruments through a catheter and into an artery or vein to evaluate the vessel and a lesion site. Such imaging modalities include intravascular ultrasound (IVUS) or optical coherence (OCT) imaging, for example. The imaging modalities provide anatomical information about the vessel and the stenosis, but not functional information. In the event a stenosis is deemed significant by a reduction in luminal diameter, an invasive functional study such as FFR or IFR would be performed to determine functional significance. IVUS and OCT imaging also increase the risk of adverse events for the patient, including major or minor bleeding, vessel perforation, vessel tearing, renal dysfunction or failure, myocardial infarction, arrhythmia, stroke, and death.

In the event that a stenosis requires revascularization, the most common method of percutaneous revascularization is to implant a coronary stent. Approximately 15-30% of patients receiving a stent develop restenosis, an exaggerated healing response to the stent placement, and often the patient with restenosis has additional coronary incidents, namely stable angina, unstable angina, myocardial infarction, arrhythmia, sudden cardiac arrest, and death. It is known that certain clinical, procedural, or angiographic features are associated with in-stent restenosis; however, none of these factors can predict in-stent restenosis at the time of implantation and many factors cannot be modified.

Interventional cardiologists employ the best clinical judgement of treatment options of coronary artery blockage based on the 2D angiography imaging. For example, stent choice (length, diameter) for insertion in the artery to cure the blockade or other surgery.

The systems and methods described herein meet a clinical need for on-site, point-of-care diagnostic and prognostic determinations using a 3D geometric computational analysis tool to enhance clinical decision making by way of evaluating fluid dynamics, such as arterial fluid dynamics and hemodynamics to identify the location, size, and extent of an arterial or venous or lymphatic blockage and the hemodynamic effects of the blockage within the context of the vessel anatomy and geometry. Clinical decision making is further enhanced by facilitating evaluation and selection of an optimal interventional method, and in the case of selecting stent placement, to assess the optimal stent, stent design, and stent placement.

The systems and methods described herein may also be applicable to any biological structure in the body through which fluid flows.

FIG. 1 depicts a simplified flow diagram of an example method 100 that may be carried out to generate a three-dimensional hemodynamic simulation of a sample, in accordance with at least one embodiment.

As referenced herein, the sample may be in a subject such as a human or nonhuman subject. The sample may be an in vivo sample.

For the method 100 and other processes and methods disclosed herein, the flowchart shows functionality and operation of one possible implementation of the present embodiments. In this regard, each block may represent a module, a segment, or a portion of program code, which includes one or more instructions executable by a processor or by a plurality of processors for implementing specific logical functions or steps in the process. In some example embodiments, a plurality of processors may work in parallel to implement the logical functions or steps in the process. The program code may be stored on any type of computer readable medium, for example, data storage including a one or more computer-readable storage media that may be read or accessed by the processor, and may be a fixed or removable hard drive, a flash memory, a rewritable optical disk, a rewritable magnetic tape, or some combination of the above. The computer readable medium may include a physical and/or non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable medium may also be any other volatile or non-volatile storage system. The computer readable medium may be considered a computer readable storage medium, a tangible storage device, or other article of manufacture, for example. Alternatively, program code, instructions, and/or data structures may be transmitted via a communications network via a propagated signal on a propagation medium (e.g., electromagnetic wave(s), sound wave(s), etc.).

Initially, the method 100 includes acquiring one or more 2D images of a sample, wherein the sample comprises a biological structure having fluid flow therethrough, at block 110.

In one example embodiment, the one or more 2D images comprise part of or an entire CT scan. In some example embodiments, the CT scan comprises a biplane coronary CT angiogram. In one example embodiment, a single 2D angiogram image may be obtained via rotational angiography and used for the method 100. In alternative embodiments, a plurality of 2D images may be obtained via various 2D imaging modalities, such as x-ray, photographs, magnetic resonance imaging (MM), lymphangiography, intravascular ultrasound (IVUS), optical coherence tomography (OCT), ultrasound (transthoracic, transesophageal, abdominal, bladder, prostate), nuclear medicine, and positron emission tomography (PET) scans, for example. Additional modalities that can be used to obtain 2D images may further be envisioned.

The method 100 then includes segmenting the image, at block 120. Image segmentation comprises partitioning the image into multiple sets (e.g., sets of pixels). Image segmentation is performed to locate objects and boundaries in the image (e.g., lines, curves) by assigning a label to every pixel in an image. Within a region of an image, pixels will have similarities with respect to certain characteristics, such as color, intensity, or texture. Adjacent regions may be significantly different with respect to the same characteristics. The method uses a pair of 2D images and parameters of the C-arm angiography gantry system (e.g., separation angles of 45 degrees, image intensifier, and pixel size, among other parameters).

In one example embodiment, a thresholding method may be used for image segmentation, wherein the edges in the image are determined via the threshold on the opacity or gray-scale of pixels. A threshold value may be used to turn a gray-scale image into a binary image. A tool such as Materialise Mimics® may be used to perform this operation.

In one example embodiment, the data obtained from segmentation may be smoothed using a prototype design tool, such as a tool capable of handling triangular meshes, such as Meshmixer®. The triangular meshes represent the 3D structure of the vessel. When working with traditional CT images or MR images, there is a 2D slice every few millimeters along the z-axis. Each 2D image is segmented to determine the outline edges in that z-plane and then the full 3D geometry is created by stitching the stack together. For the reconstruction from the 2D images, the angiograms are segmented to retrieve the vessel shape in the two angles of the angiograms. The 2D outlines are then projected into 3D space and used to create the 3D triangulated mesh.

In some embodiments, at this stage in the process, an individual, such as a physician, may choose to review and validate the data.

The method 100 then includes generating 3D geometries from the segmented data, at block 130. The 3D geometries are patient-specific geometries.

The method 100 further includes generating a three-dimensional reconstruction of the biological structure from the three-dimensional geometries, at block 140.

In some embodiments, computational fluid dynamic (CFD) simulations may further be performed to generate a three-dimensional wall shear stress (WSS) map, an/or to generate a range of macroscopic quantities such as FFR, velocity, pressure, vorticity, oscillatory shear index, and the like. In some embodiments, a HARVEY simulator, which is a fluid dynamic solver used to study macroscopic flow properties. The HARVEY simulator relies on an implementation of the Lattice Boltzmann Method (LBM), which is an alternative solver of the Navier-Stokes equations. LBM defines a fluid by a probability distribution function, $f_i$, of particles moving on a regular lattice x according to discrete velocities $c_i$. Macroscopic fluid variables, such as pressure p and velocity v, are computed locally as movements of $f_i$, (x, t). In some embodiments, the simulation parameter used by HARVEY comprises a velocity of 9 cm/s, a kinetic viscosity of 0.0004cP, an LBM viscosity of 0.0125, a resolution of 50 µm, a fluid density of 1060 kg/m$^3$, 64-128 nodes, and finite difference boundary conditions. Other parameters may be applied in alternative embodiments.

The generated 3D WSS map may be used to: (i) identify an enhanced precise location of an arterial blockage, including areas that extend beyond the visually identifiable stenosis that impact WSS (areas of low WSS stimulate neointima/neoatherosclerosis formation, which is the cause of in-stent restenosis); (ii) identify the size, geometry, and local geography of the arterial blockage; (iii) assess the fluid flow and WSS dynamic of the blockage; and (iv) determine the optimal stent design and size (e.g., diameter, length) that mitigates areas of low WSS. Once these parameters are clarified, simulations of interventional methods and clinical decision making can be made, such as opting for best interventional treatment (e.g., coronary artery bypass grafting, balloon, stent), and choosing an interventional treatment and testing the treatment in the patient specific 3D WSS map, as well as creating a 3D file that can be used to aid in generating patient-specific stents for implantation.

In a preferred embodiment, optimal stent (e.g., diameter and length) selection based on clinical expertise can be tested using the patient specific 3D WSS map simulation of the instant method and the resulting fluid flow and shear stress in the blockade location will identify the utility of the stent parameters of a specific stent for insertion (e.g., stent design, length, and diameter) as well as stent location for optimal clinical benefit.

A database of attained 3D WSS maps may be maintained, as well as clinical patient outcomes having an algorithmic machine learning component, to enhance both 3D map generation and a prediction of the location of stent placement and the optimal physical parameters of stent and utility (e.g., stent design, diameter, and length).

A sample to be imaged may comprise any structure with fluid flow therein. In some embodiments, the sample to be images comprises a vascular or lymphatic bed.

The method 100 may be used to determine wall shear stress (WSS), which may also referred to as endothelial shear stress (ESS), in the coronary artery of a subject. In some embodiments, the method 100 can be used to diagnose, or provide a prognosis for a vascular disease in a subject, or determine locations of WSS of a blood vessel wall. In some embodiments, the blood vessel is the coronary artery. In other embodiments, the method 100 can be used to determine fractional flow reserve, velocity, oscillatory shear index, pressure, time averaged-wall shear stress, density, vorticity, and vortex location and wall distance from vortex center for a fluid flow, for example. Still other parameters and data concerning fluid flow may be determined using the method 100.

The term vascular disease includes, but is not limited to, diseases such as atherosclerosis, restenosis, hypertension, arterial stiffness, vasculitis, arteritis, inflammatory or immune-related vasculitides, aneurysms, congenital anomalies of the vasculature, thromboembolic disease, post-transplant arteriopathy, post-surgical arteriopathy, as well as vascular dysfunctions associated with other localized or systemic diseases.

In one example embodiument, the method 100 provides for a non-invasive, efficient, and effective analysis of hemodynamic effects of the blockage within the context of the vessel anatomy and geometry.

In other embodiments, the method 100 may be used to model blood flow through chambers of a heart and/or across heart valves.

In further embodiments, the sample to be imaged comprises one or both of the brain and spinal cord, wherein cerebrospinal fluid may for example examined. In yet other example embodiments, the sample to be imaged can comprise an eye (for examining, e.g., vitreous humor flow), a gastrointestinal tract (for examining, e.g., the mouth, esophagus, stomach, colon, including small intestine and/or large intestine, and rectum and fluids that flow therethrough), a gallbladder (for examining, e.g., bile), kidneys, ureters, bladder, urethra (for examining, e.g., urine), a scrotum and prostate (for examining, e.g., seminal fluid), and a uterus and umbilical artery (for examining, e.g., amniotic fluid and placental blood flow).

II. Example 3D Modeling Methods

In a recent study, twenty patients underwent both coronary angiography and CT angiography within one month. Imaging data from the angiographies was acquired from the Brigham and Womens' Hospital. A double blind experiment was conducted to create patient-specific 3D arterial models from 2D angiogram and CTA data. The resulting 3D reconstructions were then validated by two cardiologists.

In the study, two 2D imaging systems, such as the imaging system 200 were used. A 3D coronary skeleton was calculated in terms of vessel centerlines and cross-sectional diameter. 3D reconstructions were obtained from 2D patient angiograms at the end of diastole, using a method such as the method 100. The CTA models were reconstructed by segmenting high resolution soft axial Dicom images with 500 μm slice thickness at 75% cardiac cycle using Mimics software. Segmentation bias was minimized by working closely with a cardiologist and validating scan regions corresponding to coronary vessels. The study was unblinded after both CTA and angiogram reconstructed models were validated by two cardiologists.

The angiogram reconstruction resulted in two types of models. The first model was a complete coronary model (CCM), wherein the 3D reconstruction algorithm enables the generation of a complete arterial tree, including all angiographically visible vessels greater than 1 mm in diameter. The second model was a matched coronary model (MCM), wherein the CCMs were matched to the respective CTA models with respect to the vessel type, number, and length.

In the present example, all geometric models were exported as mesh files in standard stereolithography file format for further geometric and CFD analysis. In other examples, a variety of other file formats may be used. The topological and anatomical validity of the angiogram models was assessed by comparing the models to corresponding CTA models from the same patient and calculating Hausdorff distance (HD) between these models. HD is a metric that quantifies geometric resemblance between 3D models. HD was computed between the MCMs and CTA models for 27 patient-specific cases. To compute HD, surface meshes derived from 3D models of CTA and coronary angiogram (CA) data were aligned using N-point registration in 3Matic, by identifying discernible features such as branching patterns. A Part Compare Analysis tool from 3Matic® was used to compute mean symmetric HD between 3D geometries from CTA and angiogram derived models.

A 3D phantom was generated using the mesh file from the 2D angiogram reconstruction. The phantom was injected with Visipaque® 320 ionic contrast dye and imaged using standard right and left coronary artery angiographic views. A 0.014 in coronary wire was included with each image to provide scale. The resulting angiogram was compared with the original angiogram from the patient to confirm the geometrical reconstruction. Cartesian distance was calculated to quantitatively compare the resulting angiogram along 10 arterial locations.

CFD simulations were then conducted using HARVEY. To model coronary circulation, blood was simulated as an incompressible Newtonian fluid with a dynamic viscosity of 4 cP and density of 1060 kg/m$^3$. The blood vessels were modeled as rigid walls with a no slip boundary condition. At the outlets, a lumped parameter model was applied using microcirculation resistance. The coronary arterial microcirculation resistance for all geometries was generated based on the vessel diameter, mean flow, and mean aortic pressure. For the present example, the inlet boundary condition a Poiseuille profile was imposed with transient flow using a velocity waveform. It is recognized that other boundary conditions may be applied. Transient (or pulsatile) simulations capture the periodically velocity during the cardiac cycle. Pulsatile WSS derived from transient simulations is thus varying in magnitude, unidirectional, and averaged over the period of the cardiac cycle.

The results of a convergence study indicate that the simulations were convergent at 50 μm resolution, with approximately $1.9 \times 10^7$ and $1.6 \times 10^7$ fluid points for CCM and MCM models, respectively. A total of 54 CFD simulations were performed for all the CCMs and MCMs with the same boundary condition at the inlet. A vessel centerline was obtained using Mimics. To analyze the ESS trend in the arterial models, a circumferential averaged ESS was computed at each point on the centerline. Local differences in ESS were assessed by performing a point-to-point comparison between the CCM and MCM models from all 27 patient-specific geometries. Each geometry was divided in sections at a distance of 0.3 mm along the centerline, resulting in approximately 2,000 sections per geometry. There were 17,757 sections common to 54 CCM or MCM models. Pressure gradient was calculated by computing pressure above and below a stenosis. Volumetric flow rate was computed at the end of the vessel.

A total of 54 angiogram and CTA models were reconstructed from 27 patient datasets. The topological accuracy of angiogram reconstructions was assessed by computing HD between angiogram models and CTA derived geometries. Symmetric HDs were calculated for each angiogram model with the CTA models derived from all patient cases.

Figure 2:
FIG. 2 depicts a table summarizing a comparison of 3D angiography with respect to a CTA model, in accordance with at least one example embodiment.

FIG. 2 depicts a table 200 summarizing a comparison of 3D angiography with respect to a CTA model, in accordance with at least one embodiment. In table 200, ten locations along the arterial tree were selected in the patient and phantom angiograms based on discernable features such as bifurcation points and stenosis. The Cartesian distance is calculated for each of the ten locations and listed in table 200. The average distance is provided in table 200 as 2.86 mm. This average distance is an order of magnitude smaller than the coronary arterial length scales. Therefore, the phantom angiogram is in close agreement with the original patient angiogram.

FIG. 3 depicts a table 300 summarizing the influence of side branches on hemodynamics, in accordance with at least one embodiment. A complex interplay exists between flow fields, arterial anatomy, and branching pattern within regions of vessel bifurcation; therefore, incorporating side branches for accurate modeling of arterial flow is desired. A side branch study was thus performed using Meshlab®, an open source meshing software, to create a corresponding left coronary (LCA) model without side branches by deleting all side vessels. The modified LCA model without side branches consisted of only the main vessels with major bifurcations: left main (LM), left anterior descending (LAD), left circumflex (LCX), diagonal 1 and obtuse marginal 1 (main vessels). To further investigate the effect of number, location and length of side branches on arterial flow, four models were generated using Meshlab® of LAD with 0, 1, 2, and 3 side branches, corresponding in table 300 to LAD 0, LAD 1, LAD 2, and LAD 3, respectively. The study of side branches emphasizes the value of using more detailed 3D geometries and higher resolution mesh for 3D fluid flow analyses.

Figure 4:
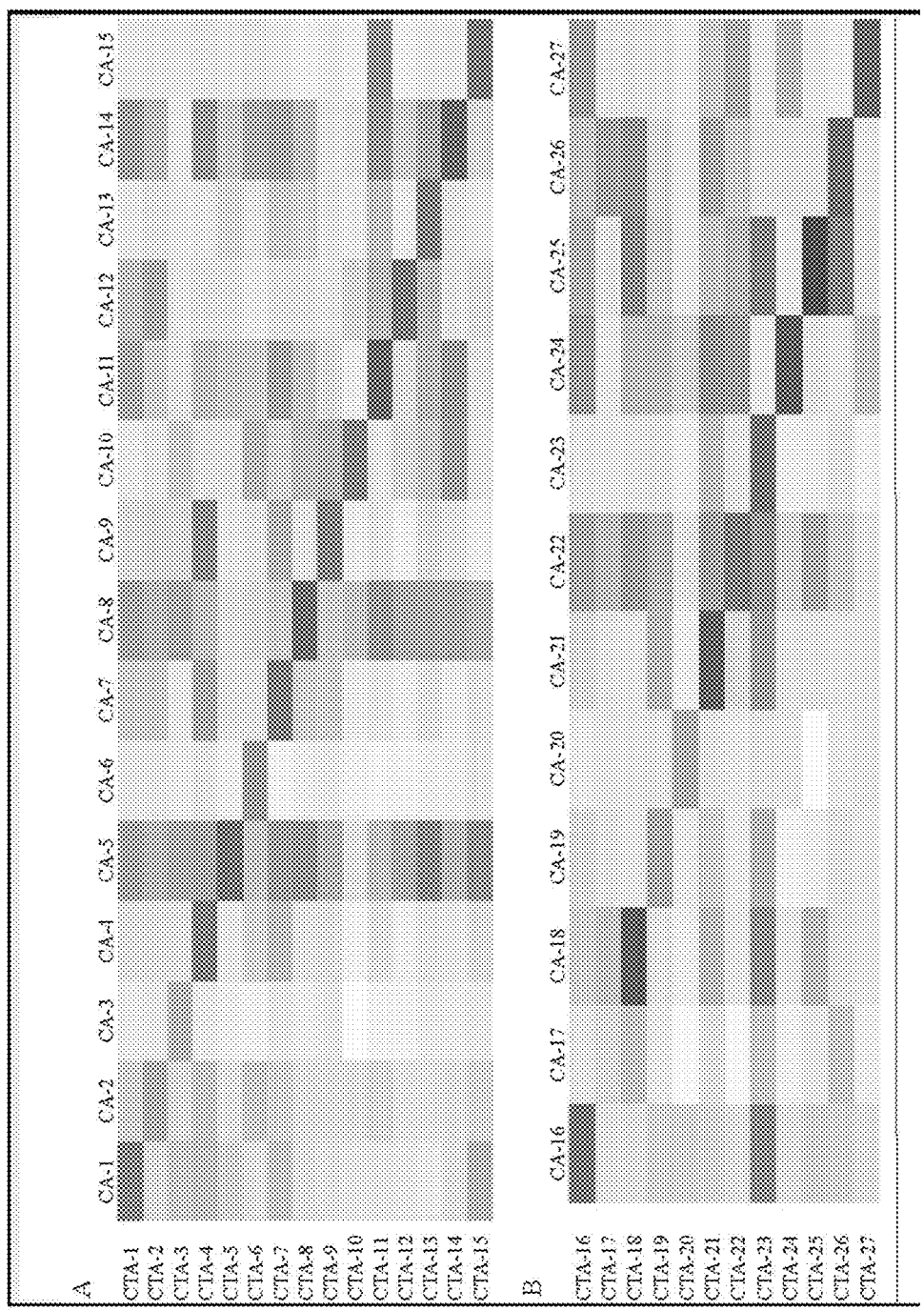
FIG. 4 depicts a Hausdorff Distance (HD) matrix comparing 3D angiography with respect to a CTA model, in accordance with at least one example embodiment.

FIG. 4 depicts an HD matrix 400 plotting coronary angiogram (CA) models on the horizontal axis and CTA models on the vertical axis, in accordance with at least one embodiment. As shown in FIG. 4, the models for all 27 patient cases are present. The matrix labeled "A" shows the heat map of the HD for the left coronary geometries. The matrix labeled "B" shows the head map of the HD for the right coronary geometries. The darker regions in the matrix 400 represent a minimum symmetric HD and thus the highest topological resemblance. The dark region along the diagonal for both A and B matrices represents correctly identified CA and CTA models from the same patient. A high topological similarity between the CTA and angiogram models shows that a complex geometry of the coronary tree can be accurately created from 2D angiograms with realistic vessel length and diameter.

Figure 5:
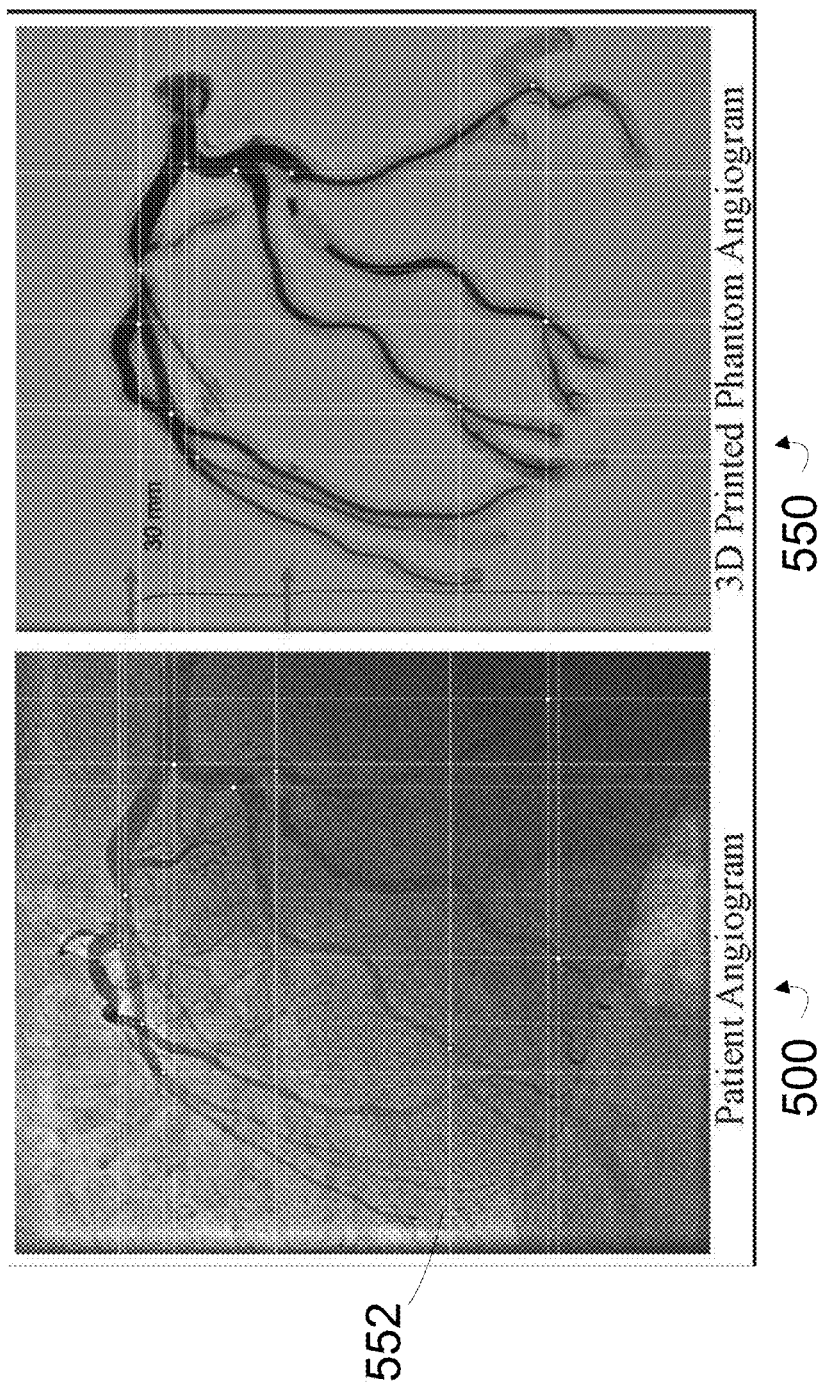
FIG. 5 depicts a 2D angiogram image and a corresponding 3D reconstruction of vessels from the 2D angiogram image, in accordance with at least one example embodiment.

FIG. 5 depicts a patient angiogram image 500 adjacent a 3D printed phantom angiogram image 550, in accordance with at least one embodiment. The image 550 may be generated via the method 100 described above, in one example embodiment. The geometric reconstruction was experimentally validated by comparing the two images, wherein the 3D printed phantom angiogram image 550 was derived from the mesh file of the angiogram reconstruction. The white cross lines 552 identify the locations that are used for computing Cartesian distance between the angiograms.

For accurate WSS comparison the inlet boundary conditions were kept consistent for the two LCA tree models and 4 LAD vessel models. The inlet flow rate used for the two LCA models with and without side branches was set to average diastole velocity (25 cm/s). The inflow rate for the LAD derived models was matched to the flow rate at the corresponding location in the 3D LCA model with all vessels. For outlet boundary conditions, resistance outlets with microcirculation resistance values were computed based on diameter, flow rate, and mean aortic pressure. A point-to-point comparison was performed along the length of LAD for the six models to compute the differences in WSS and average velocity.

Figures 6A, 6B, 6C, 6D:
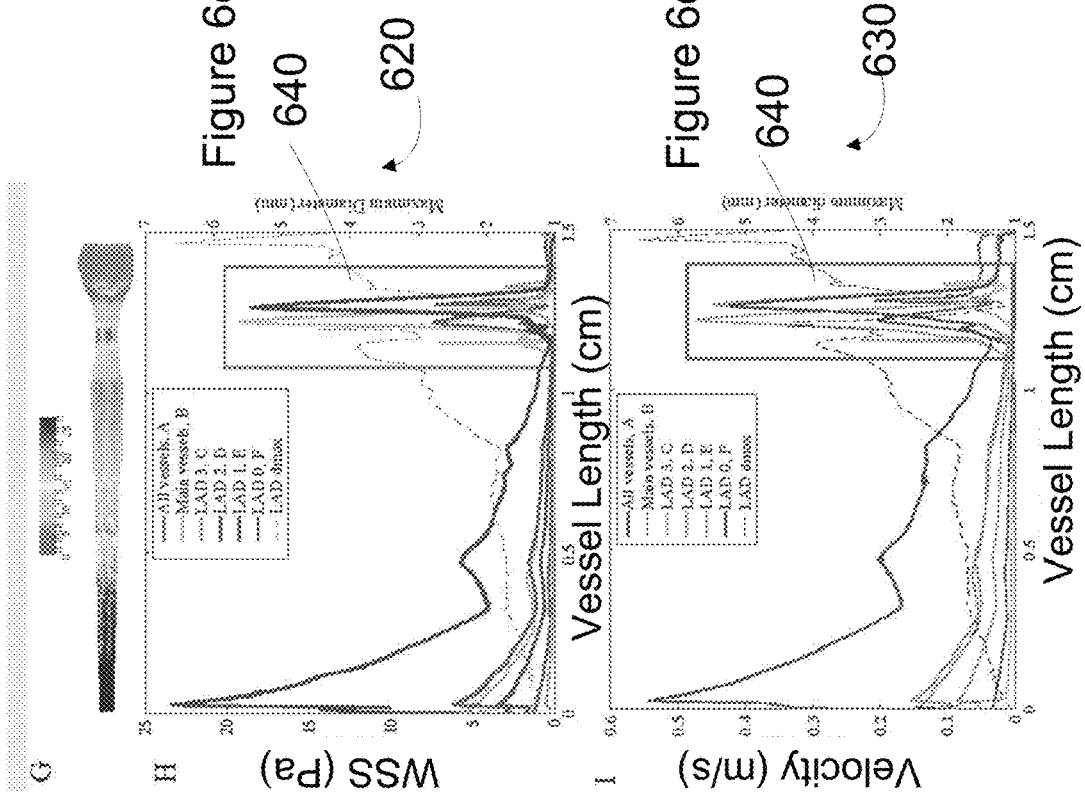
FIG. 6a depicts a model of a left coronary artery (LCA) comprising angiographically visible vessels, in accordance with at least one example embodiment.
FIG. 6b depicts a model of a left coronary artery (LCA) comprising only main vessels, in accordance with at least one example embodiment.
FIG. 6c depicts a graph plotting vessel length over wall shear stress, in accordance with at least one example embodiment.
FIG. 6d depicts a graph plotting vessel length over velocity, in accordance with at least one example embodiment.

FIG. 6a depicts a model 600 of an LCA comprising angiographically visible vessels, whereas FIG. 6b depicts a model 610 of an LCA comprising only main vessels. In the example of FIG. 6a, the angiographically visible vessels are vessels comprising a diameter larger than about 1 mm.

FIG. 6c depicts a graph 620 plotting vessel length over WSS, in accordance with one embodiment. FIG. 6d depicts a graph 630 plotting vessel length over velocity, in accordance with one embodiment. A box 640 in graphs 620, 630 marks the location of stenosis reduction in vessel diameter, where patterns of high WSS (e.g., greater than 2.0 Pa) followed by low WSS (e.g., less than 2.0 Pa) were identified. As shown in FIG. 3, average WSS in LAD 0 was 4.75 Pa and LAD 3 was 0.25 Pa, a difference of an order of magnitude. The difference in WSS arises from the overall reduction in coronary volume (0.54 ml, 25%) and sharp increase in average velocity (0.16 m/s), causing significant changes in flow distribution across different branches and thus WSS patterns in vessels.

The 3D reconstruction based on biplane angiography enables complete arterial circulation analysis of all angiographically visible vessels. Further, CCMs that take into account flow through all side branches provide for accurate computation of WSS and pressure gradient, while MCMs that have only a subset of side branches are inadequate for biomechanical studies as they overestimate Pd/Pa ratio, volumetric outflow and WSS. The 3D reconstruction based on accurate coronary physiology can improve overall fidelity of biomechanical studies to compute WSS.

The study discussed above demonstrates how the disclosed 3D reconstruction based on the conventional 2D angiogram data (which, as previously stated, is widely available) can significantly increase a target patient population, thus facilitating important advances in the biomechanical understanding of vascular diseases, such as by way of example coronary artery disease. The data derived from 3D fluid flow analyses performed using 2D images will also provide important new information not currently available to clinicians that will aid in prognosis and treatment planning.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A method for generating a three-dimensional hemodynamic simulation of a sample comprising:
   acquiring one or more two-dimensional images of a sample, wherein the sample comprises a biological vessel having fluid flow therethrough, and wherein the one or more two-dimensional images comprise a plurality of pixels, each pixel having a pixel intensity;
   segmenting data from the one or more two-dimensional images;
   locating biological boundaries within the segmented data based on whether the pixel intensity of each pixel is above or below a predetermined pixel intensity threshold;
   generating three-dimensional geometries from the segmented data based on the located biological boundaries;
   generating a three-dimensional reconstruction of the biological vessel from the three-dimensional geometries;
   generating a three-dimensional flow profile for the three-dimensional reconstruction of the biological vessel; and
   determining one or more properties from the three-dimensional flow profile, the one or more properties comprising one or more of the following: wall shear stress (WSS), velocity, vorticity, and pressure.

2. The method of claim 1, wherein the biological vessel is a blood or lymphatic vessel.

3. The method of claim 2, further comprising:
   determining locations of WSS of the blood vessel wall on the WSS map.

4. The method of claim 1, wherein acquiring one or more two-dimensional images of a sample comprises acquiring a single two-dimensional image using rotational angiography.

5. The method of claim 1, wherein the one or more two-dimensional images comprises a biplane angiogram scan.

6. The method of claim 5, wherein the biplane angiogram scan comprises a coronary CT angiogram.

7. The method of claim 1, wherein generating a three-dimensional reconstruction of the biological vessel from the three-dimensional geometries further comprises:
   generating one or more main branches of the biological vessel; and
   generating one or more side branches extending from the one or more main branches of the biological vessel.

8. The method of claim 1, wherein the method is used to diagnose, provide a prognosis, monitor treatment, or provide guidance in medical or surgical management for a vascular disorder of a subject.

9. A system for non-invasive fluid flow analysis in a biological vessel, comprising:
   an apparatus configured to generate one or more two-dimensional images from living tissue; and
   a non-transitory computer-readable medium having stored therein instructions executable to cause a computing device to perform functions to extract tissue motion from the generated images, the functions comprising:
   acquiring one or more two-dimensional images of a sample, wherein the sample comprises a biological vessel having fluid flow therethrough, and wherein the one or more two-dimensional images comprise a plurality of pixels, each pixel having a pixel intensity;
   segmenting data from the one or more two-dimensional images;
   locating biological boundaries within the segmented data based on whether the pixel intensity of each pixel is above or below a predetermined pixel intensity threshold;
   generating three-dimensional geometries from the segmented data based on the located biological boundaries;
   generating a three-dimensional reconstruction of the biological vessel from the three-dimensional geometries;
   generating a three-dimensional flow profile for the three-dimensional reconstruction of the biological vessel; and
   generating a three-dimensional wall shear stress (WSS) map for the biological vessel by applying a computational fluid dynamics (CFD) simulation to the three-dimensional reconstruction of the biological vessel.

10. The system of claim 9, the functions further comprising:
    determining locations of WSS of the biological vessel wall on the WSS map.

11. The system of claim 9, wherein the biological vessel is a blood vessel.

12. The system of claim 11, wherein the blood vessel is a coronary artery.

13. The system of claim 9, wherein the one or more two-dimensional images comprises at least a portion of one of the following: an x-ray, a photograph, an ultrasound image, an OCT image, a magnetic resonance imaging (MRI) scan, a positron emission tomography (PET) scan, and a coronary CT angiogram.

14. The system of claim 9, the functions further comprising:
    generating one or more main branches of a biological vessel; and generating one or more side branches extending from the one or more main branches of the biological vessel.

15. The system of claim 9, wherein the system is used to diagnose, monitor, or provide a prognosis for a disease in a subject for one or more of the following biological structures:
    an eye, a gastrointestinal tract, a gallbladder, a kidney, a ureter, a bladder, a urethra, a scrotum, a prostate, a uterus, and an umbilical artery.

16. The system of claim 9, wherein the system is used to diagnose a vascular disease in a subject or determine locations of WSS of a blood vessel wall.

17. The system of claim 16, wherein the system is used to provide a prognosis for a vascular disease in a subject or determine locations of WSS of a blood vessel wall.

* * * * *